US009064044B2

(12) United States Patent
Antinoro et al.

(10) Patent No.: US 9,064,044 B2
(45) Date of Patent: Jun. 23, 2015

(54) CUSTOMIZING DIAGNOSTIC CODES AND DESCRIPTIONS FOR AN ECG MANAGEMENT SYSTEM (75) Inventors: Robert Antinoro, Newbury Park, CA (US); Siddharth Bhavsar, Thousand Oaks, CA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 581 days.

(21) Appl. No.: 12/529,727

(22) PCT Filed: Mar. 4, 2008

(86) PCT No.: PCT/US2008/055777
§ 371 (c)(1),
(2), (4) Date: Sep. 3, 2009

(87) PCT Pub. No.: WO2008/109593
PCT Pub. Date: Sep. 12, 2008

(65) Prior Publication Data
US 2010/0115002 A1    May 6, 2010

Related U.S. Application Data (60) Provisional application No. 60/893,451, filed on Mar. 7, 2007.

(51) Int. Cl.
*G06F 17/30* (2006.01)
*G06F 19/00* (2011.01)

(52) U.S. Cl.
CPC .......... *G06F 19/3487* (2013.01); *G06F 19/324* (2013.01); *G06F 19/3406* (2013.01)

(58) Field of Classification Search
CPC ................... G06F 17/30707; G06F 17/30601; G06F 17/3071; G06F 17/30705; G06F 17/30864; G06F 17/30734; G06F 17/30289; G06F 17/30731
See application file for complete search history.

(56) References Cited

U.S. PATENT DOCUMENTS

| | | | |
|---|---|---|---|
| 5,410,704 A * | 4/1995 | Norden-Paul et al. | 718/101 |
| 6,004,276 A | 12/1999 | Wright et al. | |
| 6,336,900 B1 | 1/2002 | Alleckson | |
| 6,507,837 B1 * | 1/2003 | De La Huerga | 1/1 |
| 6,621,918 B1 | 9/2003 | Hu et al. | |
| 6,704,747 B1 * | 3/2004 | Fong | 1/1 |
| 6,893,396 B2 | 5/2005 | Schulze et al. | |
| 7,107,253 B1 * | 9/2006 | Sumner et al. | 706/45 |
| 7,122,005 B2 | 10/2006 | Shusterman | |
| 7,181,017 B1 * | 2/2007 | Nagel et al. | 380/282 |
| 2003/0069480 A1 * | 4/2003 | Ng et al. | 600/300 |
| 2003/0097077 A1 * | 5/2003 | Morganroth | 600/509 |
| 2003/0131024 A1 * | 7/2003 | de la Huerga | 707/200 |
| 2003/0167189 A1 * | 9/2003 | Lutgen et al. | 705/3 |

(Continued)

*Primary Examiner* — Angelica Ruiz (57) ABSTRACT

An ECG data management system is provided which enables a hospital to standardize on a preferred set of diagnostic ECG codes and descriptors which are used with a variety of different ECG recording devices such as cardiographs, defibrillators, and patient monitors. A system administrator creates a preferred set of ECG codes and descriptors, preferably by editing a comprehensive general list of such codes and descriptors. The ECG codes of the ECG devices used by the hospital are mapped to the preferred codes. Reports produced by the management system are then produced which use the ECG codes preferred by the facility. Users may also create and maintain a favorites list of their own personal ECG codes and recall and use a favorites list during editing of an ECG report.

14 Claims, 13 Drawing Sheets

(56) References Cited

U.S. PATENT DOCUMENTS

| | | |
|---|---|---|
| 2004/0025030 A1* | 2/2004 | Corbett-Clark et al. ...... 713/186 |
| 2004/0059744 A1* | 3/2004 | Duncan et al. ................ 707/102 |
| 2004/0128165 A1* | 7/2004 | Block et al. ...................... 705/2 |
| 2005/0033592 A1* | 2/2005 | Uy et al. ............................ 705/1 |
| 2005/0278290 A1* | 12/2005 | Bruce et al. ...................... 707/1 |
| 2006/0004870 A1* | 1/2006 | Pomeroy et al. ........... 707/104.1 |
| 2006/0080347 A1* | 4/2006 | Potts et al. ................... 707/101 |
| 2006/0184056 A1* | 8/2006 | de Chazal et al. ............ 600/509 |
| 2006/0190439 A1* | 8/2006 | Chowdhury et al. ............. 707/3 |
| 2006/0247545 A1* | 11/2006 | St. Martin ..................... 600/509 |
| 2007/0118550 A1* | 5/2007 | Yang et al. .................... 707/102 |
| 2007/0162308 A1* | 7/2007 | Peters ................................ 705/2 |
| 2007/0180020 A1* | 8/2007 | Woods .......................... 709/203 |
| 2007/0250352 A1* | 10/2007 | Tawil ............................... 705/4 |
| 2007/0265533 A1* | 11/2007 | Tran .............................. 600/481 |
| 2008/0109254 A1* | 5/2008 | Ganesh et al. .................... 705/2 |

* cited by examiner

CUSTOMIZING DIAGNOSTIC CODES AND DESCRIPTIONS FOR AN ECG MANAGEMENT SYSTEM

This invention relates to ECG data management systems and, in particular, to standardizing diagnostic codes and code descriptions in a facility which uses a variety of ECG recording and diagnostic instruments.

Large hospitals and clinics routinely handle a large volume of patient ECG records. ECG measurements may be acquired with a wide variety of diagnostic instruments such as cardiographs, Holter monitors, defibrillator/monitors, and patient monitoring systems. These ECG recording must be reviewed and diagnoses made to guide an appropriate course of therapy and treatment for patients. When the ECG recording are read, a diagnostician will code his or her findings and diagnosis, using diagnostic codes and code descriptors that are stored on the diagnostic device. At times the ECG recording may be automatically populated with codes produced from an analysis performed by the device itself. The codes will find their way into diagnostic reports on the ECG data, which are used by clinicians in determining courses of treatment for patients. The clinician can quickly scan the coded diagnosis and rapidly acquire an understanding of the patient's condition as revealed by the ECG data.

Unfortunately, there is no general standardization of these codes and their descriptions. Instead, each manufacturer of an ECG device will program in lists of codes that the manufacturer believes will be most suitable for characterizing the data provided by its device. The number of such codes and descriptors can be in the dozens or even in the hundreds. While many such codes are common across many ECG device vendors, there are many codes and descriptors which are unique to each device manufacturer. A large hospital or clinic which utilizes ECG devices from a number of different manufacturers is thus forced to deal with different ECG reports using different and at times conflicting codes and descriptions for the same or similar diagnostic characteristic. This proliferation and overlap of non-standardized ECG coding can lead to confusion and inefficiency in institutions where clinicians are forced to deal with devices and reporting styles of different vendors. Accordingly it is desirable to enable the medical facility to conform to the usage of a limited or single group of diagnostic ECG codes and descriptors which characterize the reports of all of the different ECG devices employed by the facility.

In accordance with the principles of the present invention, an ECG management system is provided which manages data from a variety of ECG devices. A system administrator can set up a standard list of diagnostic ECG codes and associated descriptive text to be used by a medical facility. The management system is responsive to the ECG codes provided by the ECG devices of the facility and maps unique manufacturer-supplied ECG codes to the ECG codes and statements used by the facility. Diagnostic reports can be produced using the ECG codes and statements standardized for the facility. In accordance with a further aspect of the present invention, users of the system can create and select personal lists of preferred ECG codes most frequently used in their medical practice areas.

Figure 1:
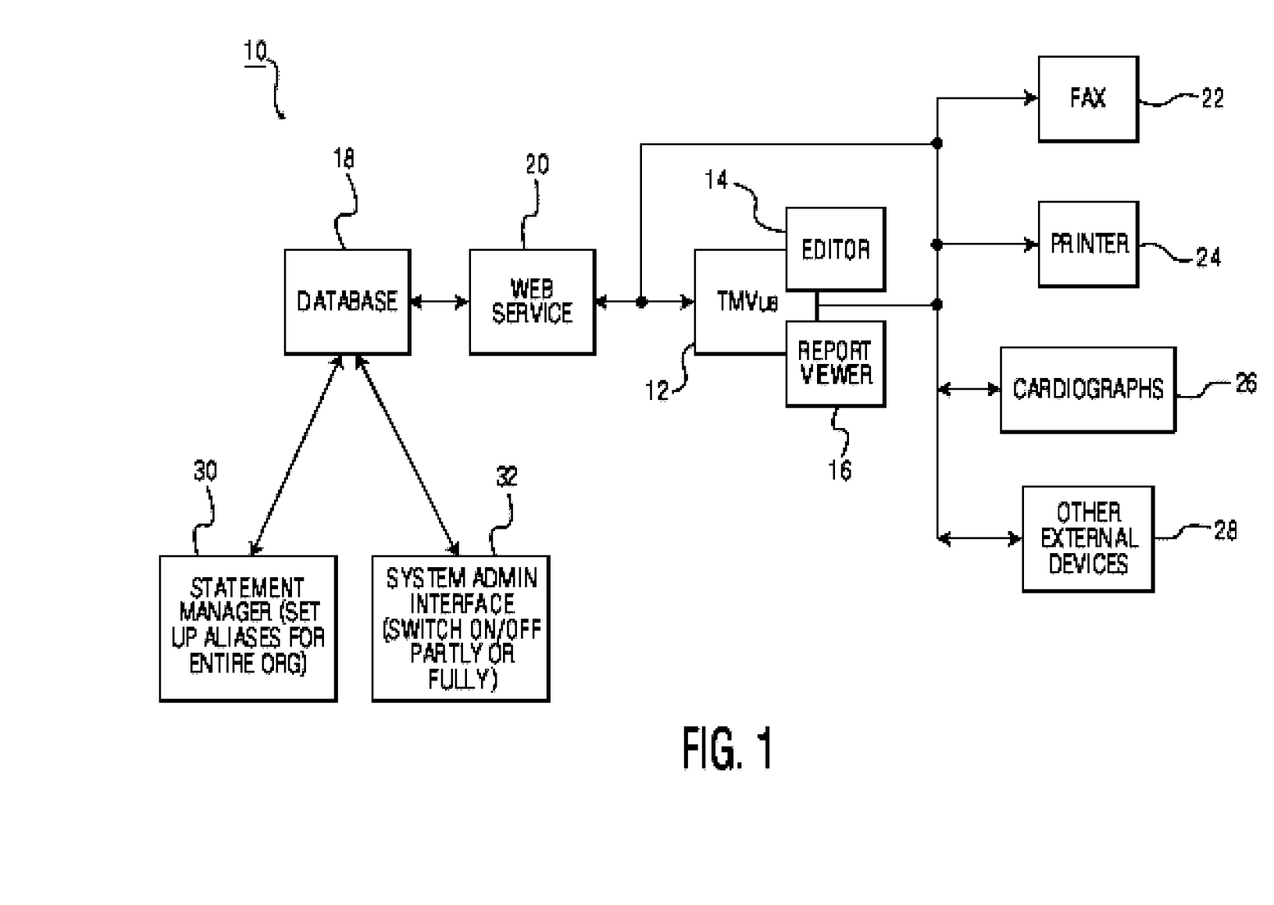
FIG. 1 illustrates in block diagram form an ECG data management system as implemented in a hospital or other medical facility.

Referring first to FIG. 1, an ECG data management system 10 as typically implemented in a hospital or other medical facility is shown in block diagram form. Usually the ECG data management system is implemented as an adjunct to the hospital information system and is accessible by users throughout the hospital's local network. The TraceMasterVue ECG management system ("TMVue" system) available from Philips Medical Systems of Andover, Mass. is typical of such systems and is used in the illustrated embodiment of the present invention. The TMVue system 12 includes a report viewer 16 which is a mode of operation by which the system renders an ECG report on a display screen. While it is displayed the report can be viewed by a physician, transmitted to other locations on the network, or modified or edited by use of an editor 14. In accordance with the principles of the present invention the editor 14 is able to access a database 18 of diagnostic codes and corresponding descriptions of the codes, referred to herein as "statements," by means of an Internet-compatible interface, Web service 20. Finished ECG reports can be faxed from a fax 22 or printed on a printer 24 connected to the system. The TMVue system 12 can receive ECG data such as a cardiogram or an ECG report generated from cardiographs 26 The TMVue system 12 can also receive ECG data and ECG reports from other devices 28 such as patient monitors and defibrillators.

An ECG data management system such as the TraceMasterVue system is generally shipped from the manufacturer with a factory-provided list of ECG diagnostic codes and statements. A typical list can contain approximately 600 codes which can be used by clinicians to characterize an ECG trace and are entered into an ECG report. However the ECG data management system is intended to handle ECG data and reports from all sources available to the hospital, including cardiographs, patient monitors, and defibrillators made by a variety of manufacturers. Each manufacturer will provide its ECG data with codes chosen by and sometimes unique to that manufacturer or device. In the case of cardiographs, these devices also include algorithms which automatically interpret characteristics of the ECG data acquired by the cardiograph and send ECG reports from the cardiograph with diagnostic codes and statements provided by the device. Frequently the codes and statements in the reports produced by the cardiograph will be different from or even conflict with the codes and statements of the list which is resident in the ECG data management system. Thus, different users of the ECG data management system can produce or receive ECG reports with differing diagnostic codes and statements and reports from different sources which use similar or identical codes for the same diagnostic characteristic. The proliferation of these different and conflicting diagnostic codes throughout the hospital can lead to confusion and misinformation among the medical staff of the facility.

In accordance with a first aspect of the present invention, the factory-supplied list of diagnostic ECG codes and statements of the ECG data management system can be edited and modified to produce a common list of codes and statements which are used in ECG reports throughout the facility and for all device data. Furthermore, the common list can be edited to contain codes and statements that are uniquely defined or used by the hospital. This means that all clinicians will be exchanging the same diagnostic information for the same diagnostic characteristics, and can also use codes and statements that are unique to their practice or preferred in a particular facility. Clinicians will no longer have to deal with reports from different sources which use different or conflicting codes for the same characteristics. The ECG data management system of FIG. 1 includes a statement manager 30 by which a system administrator can review the factory-supplied list of diagnostic codes and statements, and edit the list so that it contains codes and statements which are preferred by the facility. By this editing the administrator is able to edit out codes which are not used by the facility, redefine existing codes and also create new codes which are unique to the hospital. Edited codes are referred to as "aliases" in the following discussion. In a constructed embodiment of the present invention the administrator is able to do this editing either online or offline with respect to the ECG data management system. Once the administrator has edited the list, the codes and statements of the edited list can be implemented across the system for all users by a system administration interface 32, and example of which is shown in FIG. 3 below.

Figure 2A:
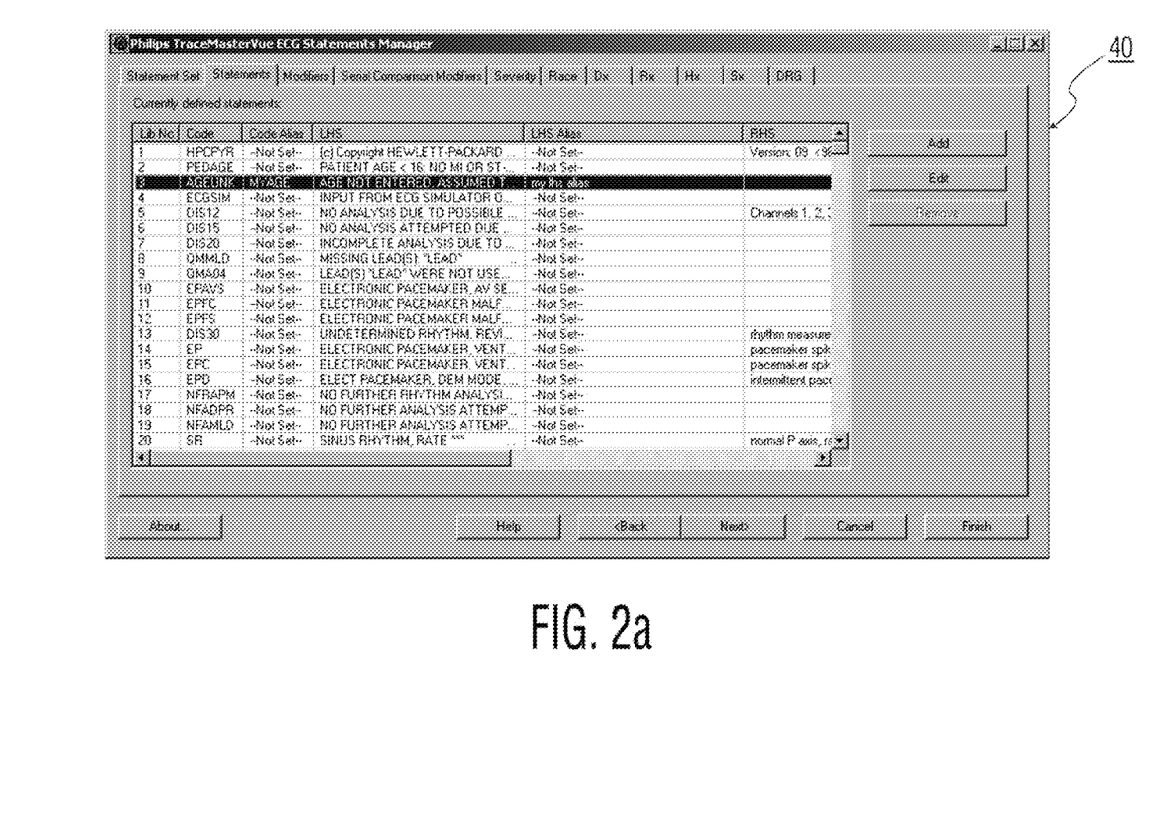
FIGS. 2a, 2b, and 2c illustrate a display screen and dialog boxes of a portion of an ECG data management system which enables creation of a customized list of diagnostic codes and associated descriptive statements for a medical facility in accordance with the present invention.
Figure 2B:
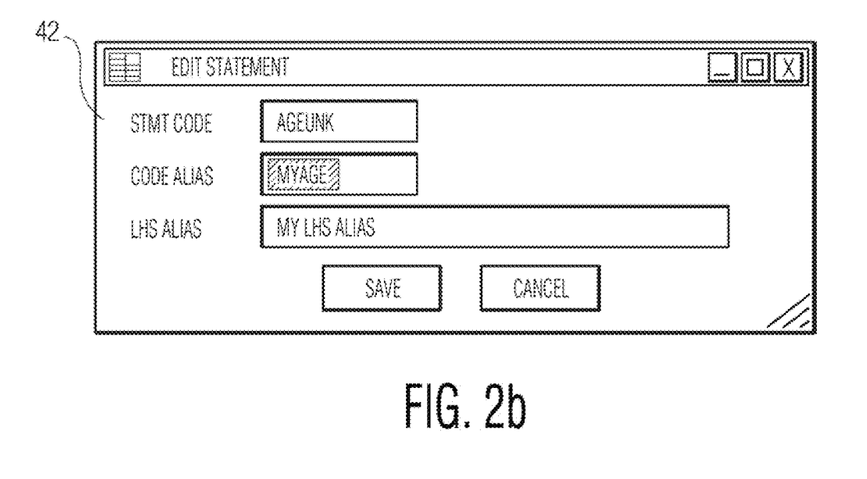

FIGS. 2a-2c illustrate how the system administrator may edit a list 40 of ECG codes and statements. In the of FIG. 2a the ECG codes and statements of the ECG data management system are sequentially numbered in the left column headed "Lib No." The second column, headed "Code," shows the code provided by the ECG data management system. The third column, headed "Code Alias," identifies whether the factory-provided code has been replaced with a custom (alias) code. This example shows that factory-provided codes 1, 2 and 4-20 have not been modified, and that the code "AGEUNK" has been replaced by an alias code "MYAGE" which the hospital prefers for this characteristic. The fourth column, headed "LHS," shows the left-hand side of the descriptive statement used for the factory-provided code "AGEUNK." The factory-provided statement can be used with the alias code "MYAGE," or the administrator can enter a custom statement in the "LHS Alias" column. In this example the administrator has entered the statement "my lhs alias" as the custom statement to be used with the alias code "MYAGE." In this example the administrator enters the alias codes and statements by double-clicking on the factory-provided code or statement in the list, which opens up a dialog box for data entry. FIG. 2b illustrates a dialog box 42 for entering an alias statement in the "LHS Alias" column. The administrator types in the alias statement in the LHS Alias window.

Figure 2C:
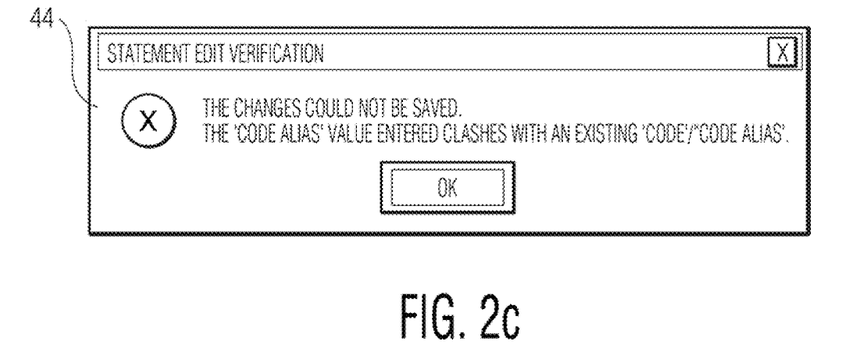

It is possible that the system administrator may try to enter an alias code that conflicts with (is the same as) a code which is already in the list 40. If that happens, the system pops up a warning box 44 as shown in FIG. 2c. In this example the warning box informs the administrator that the alias code just entered conflicts with one currently on the code list 40. The administrator can respond to this warning by deleting or changing the existing code, then entering the desired alias code.

Figure 3:
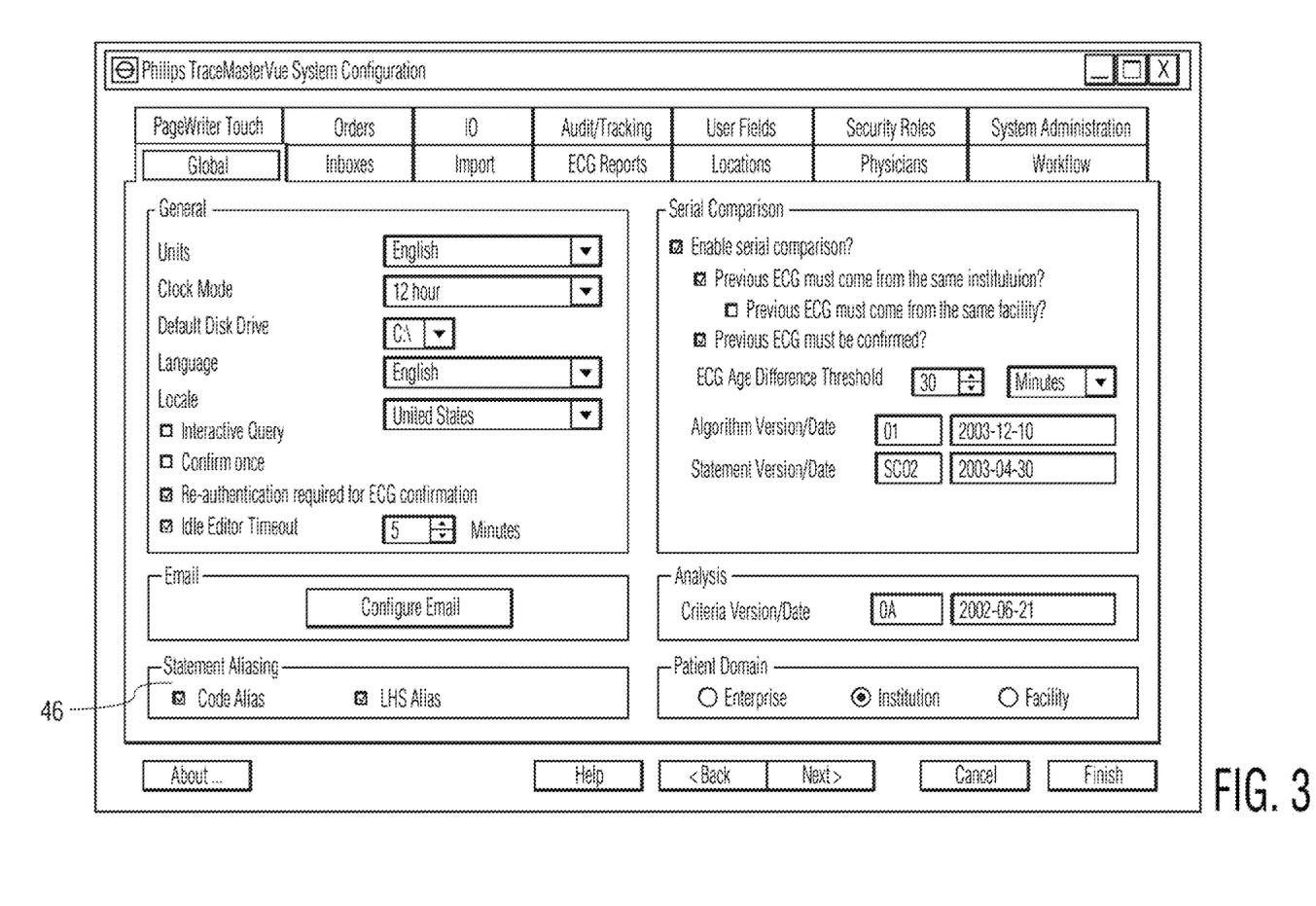
FIG. 3 illustrates a display screen of an ECG data management system which implements a customized list of diagnostic codes and statements.

Once the system administrator has modified the code and statement list as desired, the modified list can be implemented across the ECG data management system by checking the "Statement Aliasing" box 46 on the system's configuration screen as shown in FIG. 3. In this example the administrator has the option of implementing the aliased codes and the aliased statements separately if desired. For example, the administrator may have changed some of the factory-provided codes, but wants to retain and use the statements provided by the factory. In that case the administrator would only check the "Code Alias" box on the left.

Once the list of modified codes is implemented in the system, the alias codes are mapped to factory-supplied codes which they replace, as illustrated by FIG. 2a. When a device provides data or a report using a factory-supplied code which has been aliased, the factory-supplied code is replaced with the alias code and its corresponding statement when data or a report from that device is entered into the system. For instance, following the previous example, if a cardiograph produces a report which uses the code "AGEUNK" and the report is entered into the ECG data management system, the system will use the code mapping to automatically replace the factory code "AGEUNK" with the alias code "MYAGE." The report will likewise show the alias statement "my lhs alias." A reader or recipient of the report will thus see the code "MYAGE," which has been adopted by the system administrator for use in the medical facility in place of the factory-supplied code "AGEUNK."

Figure 4:
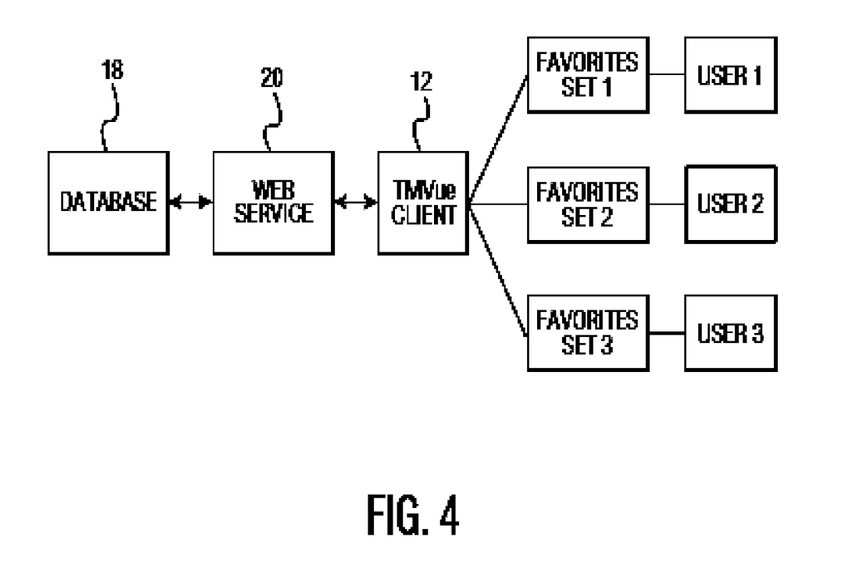
FIG. 4 is a block diagram illustrating the creation of lists of preferred codes to be used by different clinicians for ECG diagnosis and reporting.

In accordance with a further aspect of the present invention, a user of an ECG device or the ECG data management system can have a customized list of "favorite" codes provided by the ECG data management system. The favorites list contains the codes and statement which are regularly used by that person in his or her medical practice specialty. Referring to FIG. 4, the database 18 containing code and statement lists including the system-wide master list 40 is accessed by the TMVue client 12 over Web service interface 20. A user can access the master list and from it can prepare a favorites set 1, 2, or 3 of codes and statements preferred and used by that user. Users 1, 2, and 3 can each access their own favorites set 1, 2, or 3 when using the ECG data management system 10.

Figure 5:
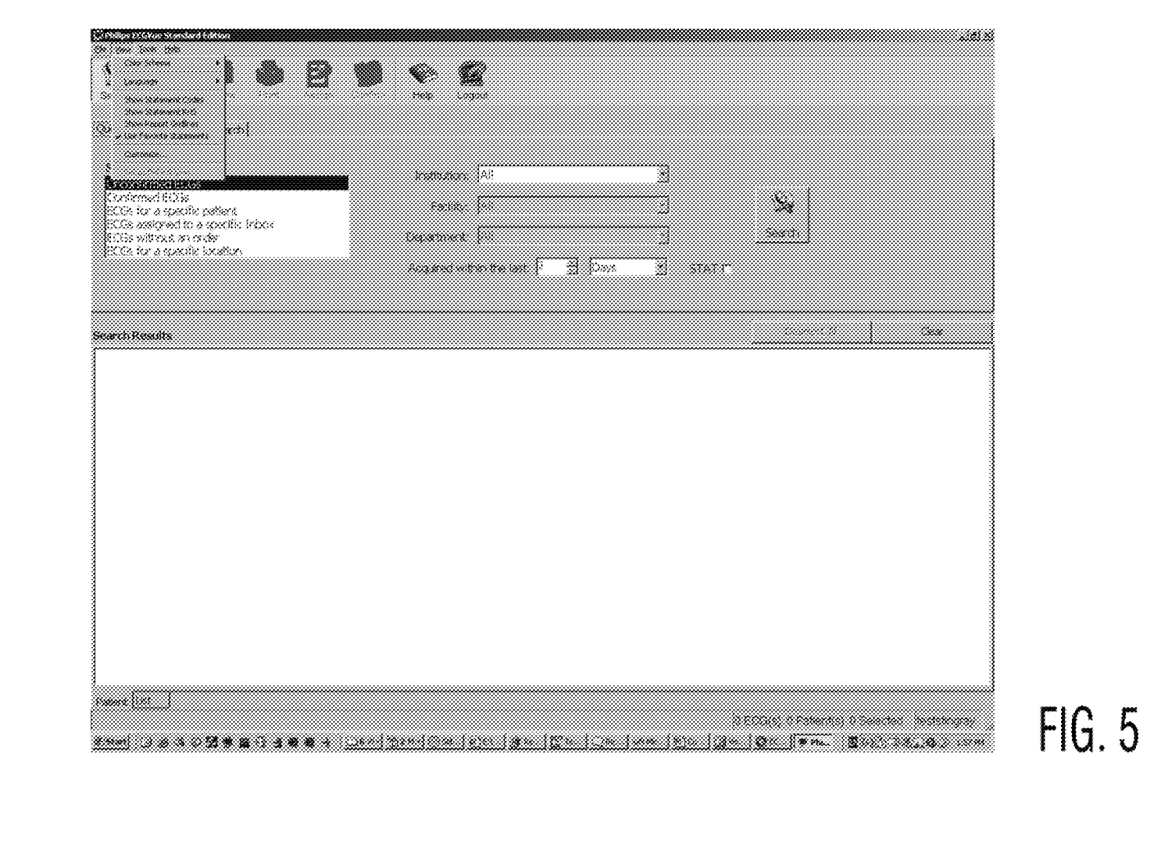
FIG. 5 illustrates a display screen of an ECG data management system which is used to set up a list of preferred diagnostic codes.

When a user wants to set up his or her own favorites list the user can begin as illustrated in FIG. 5. In this example the user has pulled down the View menu of a user screen and has checked the line "Use Favorite Statements." This selection will cause the system to facilitate the creation and use of a favorites list by the user. When this selection is set, the ECG data management system will automatically use the user's favorites list each time the user logs onto the system.

Figure 6:
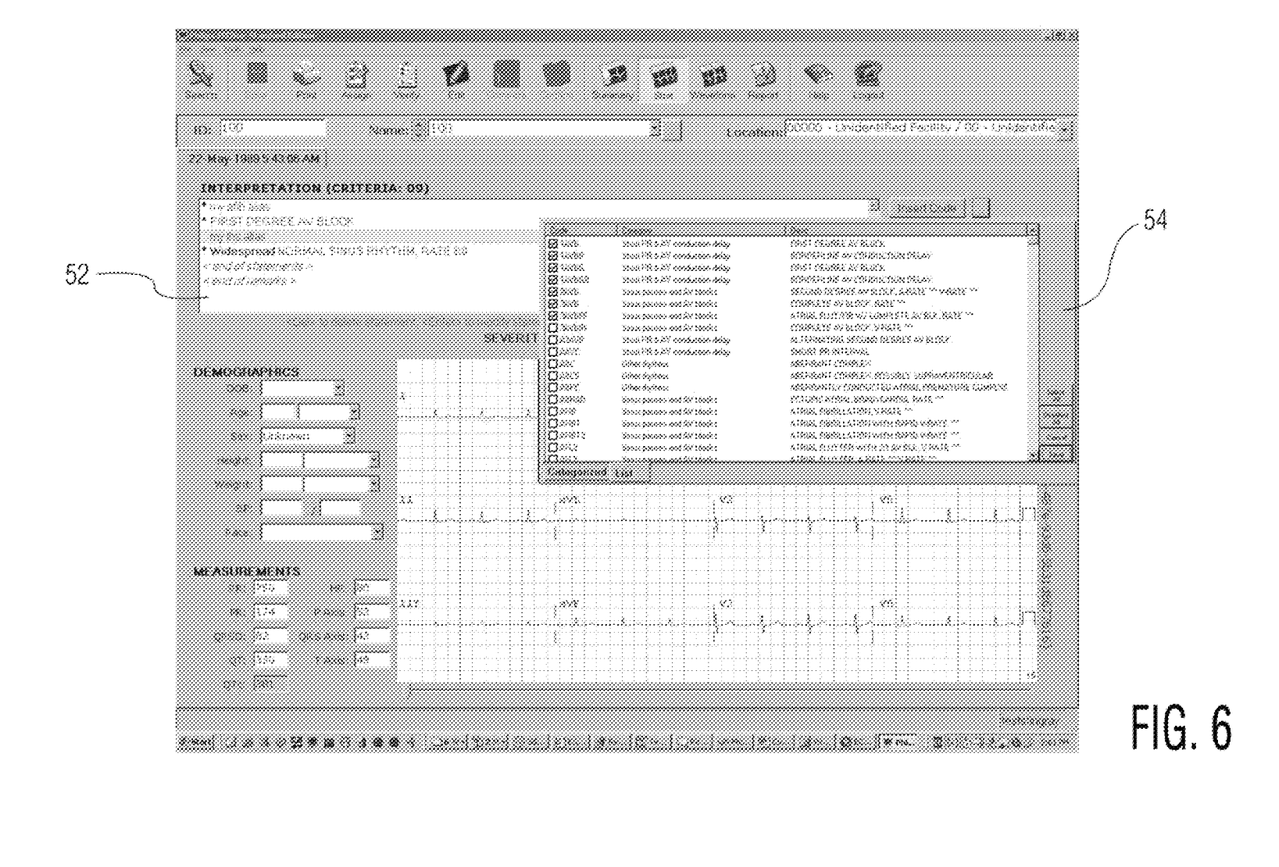
FIG. 6 illustrates a display screen of an ECG data management system in which a preferred list of diagnostic codes is being edited in accordance with the present invention.
Figure 7:
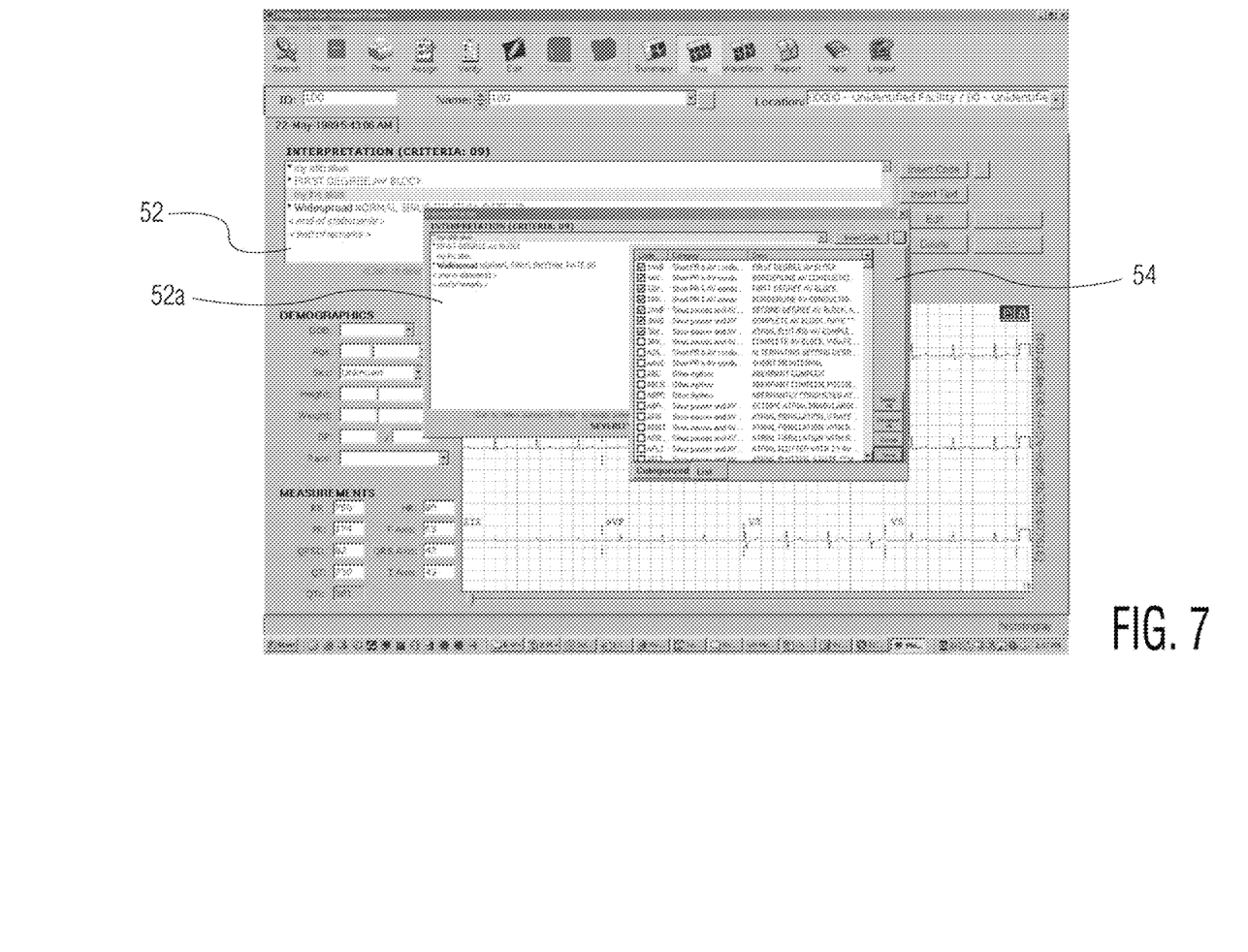
FIG. 7 illustrates a display screen of an ECG data management system in which a number of codes have been selected for a preferred list of diagnostic codes from an interpretation dialog box.

FIG. 6 shows in the background a "statement view" screen of an ECG data management system. In this view the diagnosis of the ECG traces at the bottom of the screen is presented by the dialog statements associated with ECG codes of the system. These statements are presented in an interpretation box 52 above the ECG information. In the foreground of this drawing is a selection box 54 which the user has opened to view and select ECG codes and statements for his or her favorites list. This example shows the master list of codes and statements with small check boxes at the beginning of each line. The user adds a code and statement to a favorites list by checking these boxes. As this example shows the user in this instance has checked the first seven codes and statements for use in a favorites list. The user can check additional boxes or uncheck previously checked boxes to add or delete codes and statements from the favorites list. Once the user has prepared the selections to his or her liking, the Save button in the lower right corner of the selection box is clicked to save the favorites list. FIG. 7 illustrates the statement view screen with an interpretation dialog box 52a open on the screen. In this example the user was using the interpretation dialog box to prepare a diagnostic description of the ECG information on the main screen and has needed to edit his favorites list for the diagnosis. This example shows the favorites selection box 54 being opened from the interpretation dialog box 52a, enabling the user to make modifications to a favorites list as needed even in the course of a diagnosis.

Figure 8:
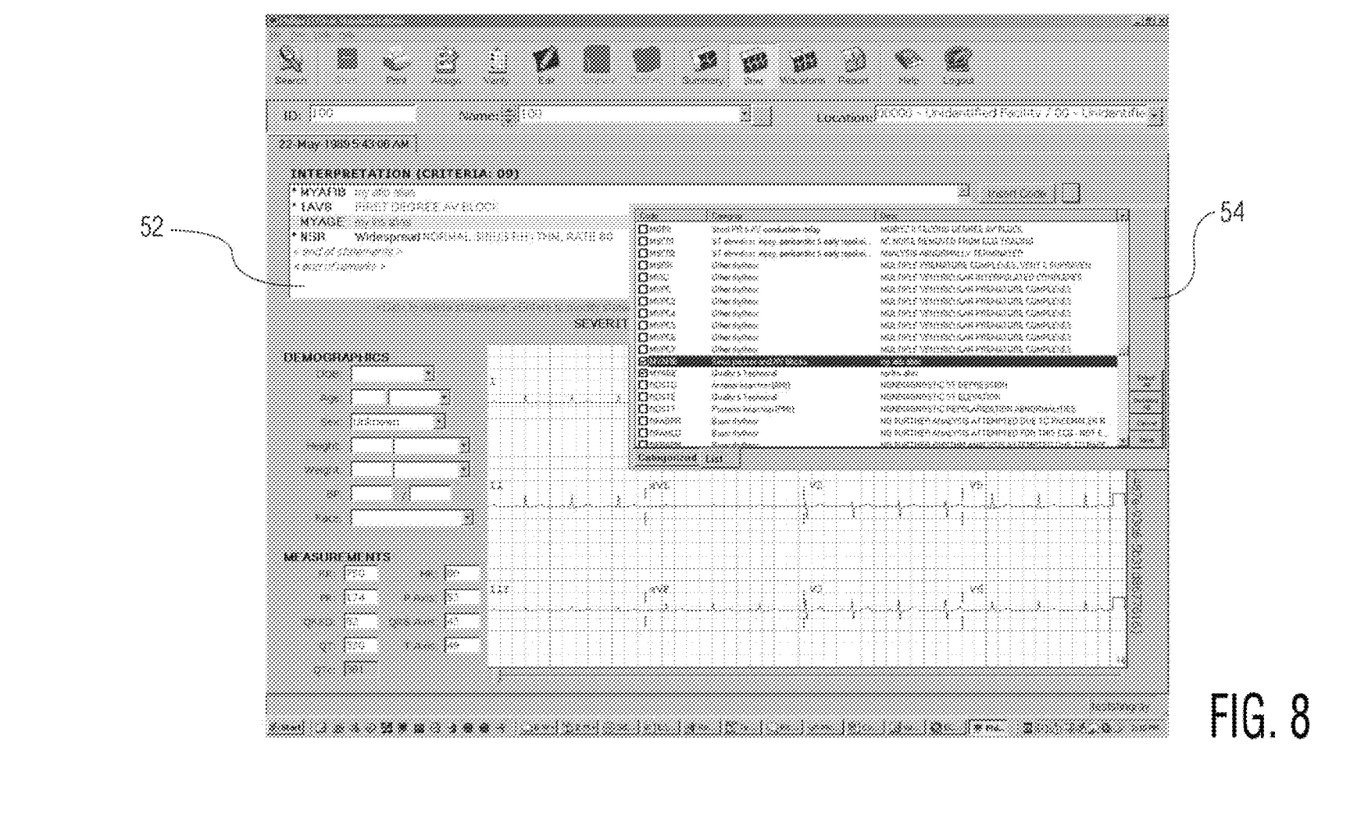
FIG. 8 illustrates a display screen of an ECG data management system in which a customized code is used in a preferred list of diagnostic codes in accordance with the present invention.
Figure 9:
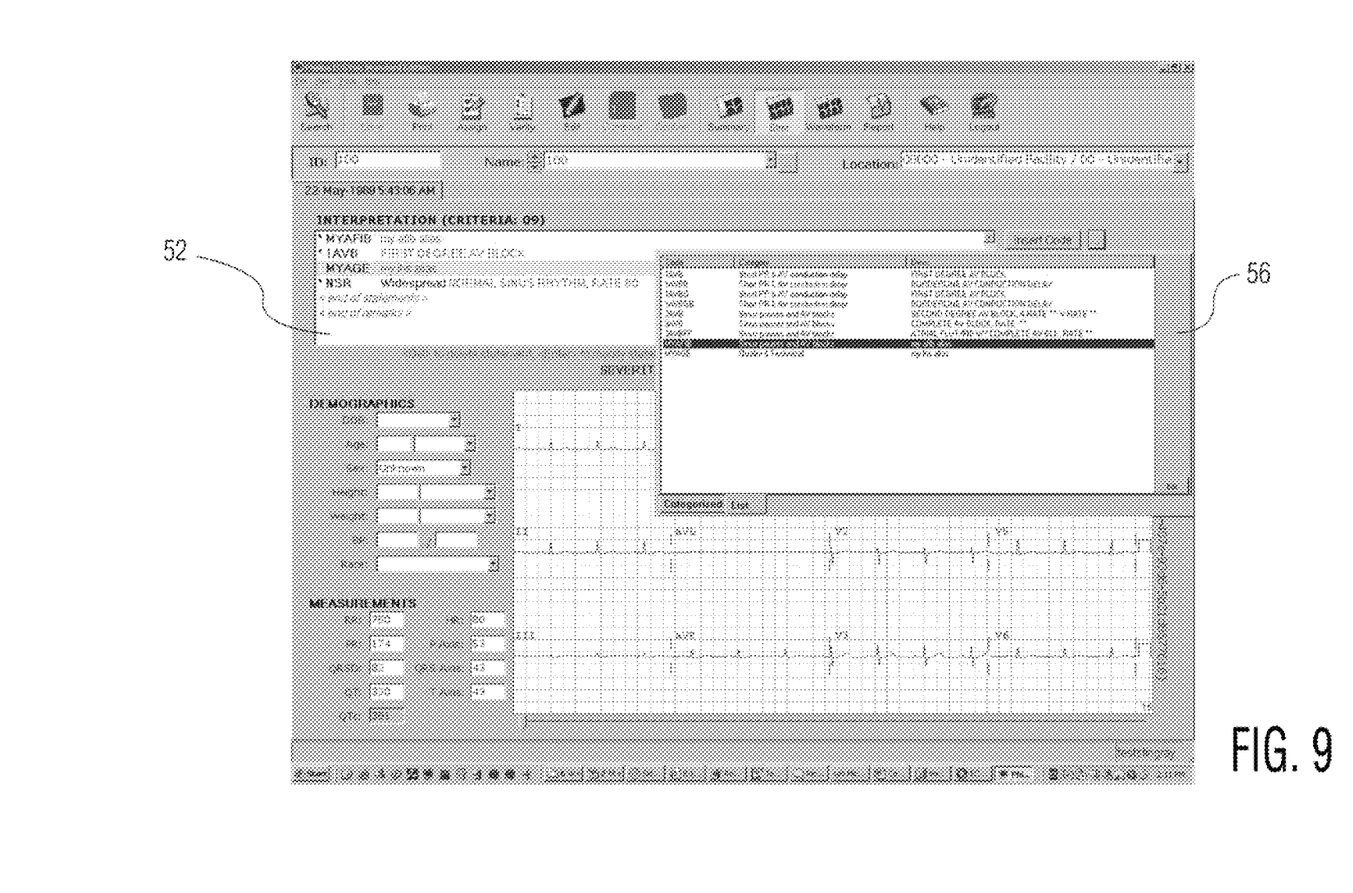
FIG. 9 illustrates a display screen of an ECG data management system in which a customized codes in a list of preferred codes is being added to the ECG interpretation by clicking on the code.

FIG. 8 shows another example of favorites list editing, in this case with the main (background) screen in report view. In this view the interpretation box 52 contains both the diagnostic ECG codes and the associated statements. The favorites selection box 54 which is open shows that this user has selected two alias (custom) codes for the favorites list, MYAFIB and MYAGE. In FIG. 9 the user has closed the selection box 54 which causes the favorites box 56 to reappear. This example shows that the user has prepared a favorites list which includes seven factory-provided codes and statements (the first seven in the list), and the two alias codes and statements, MYAFIB and MYAGE.

Figure 10:
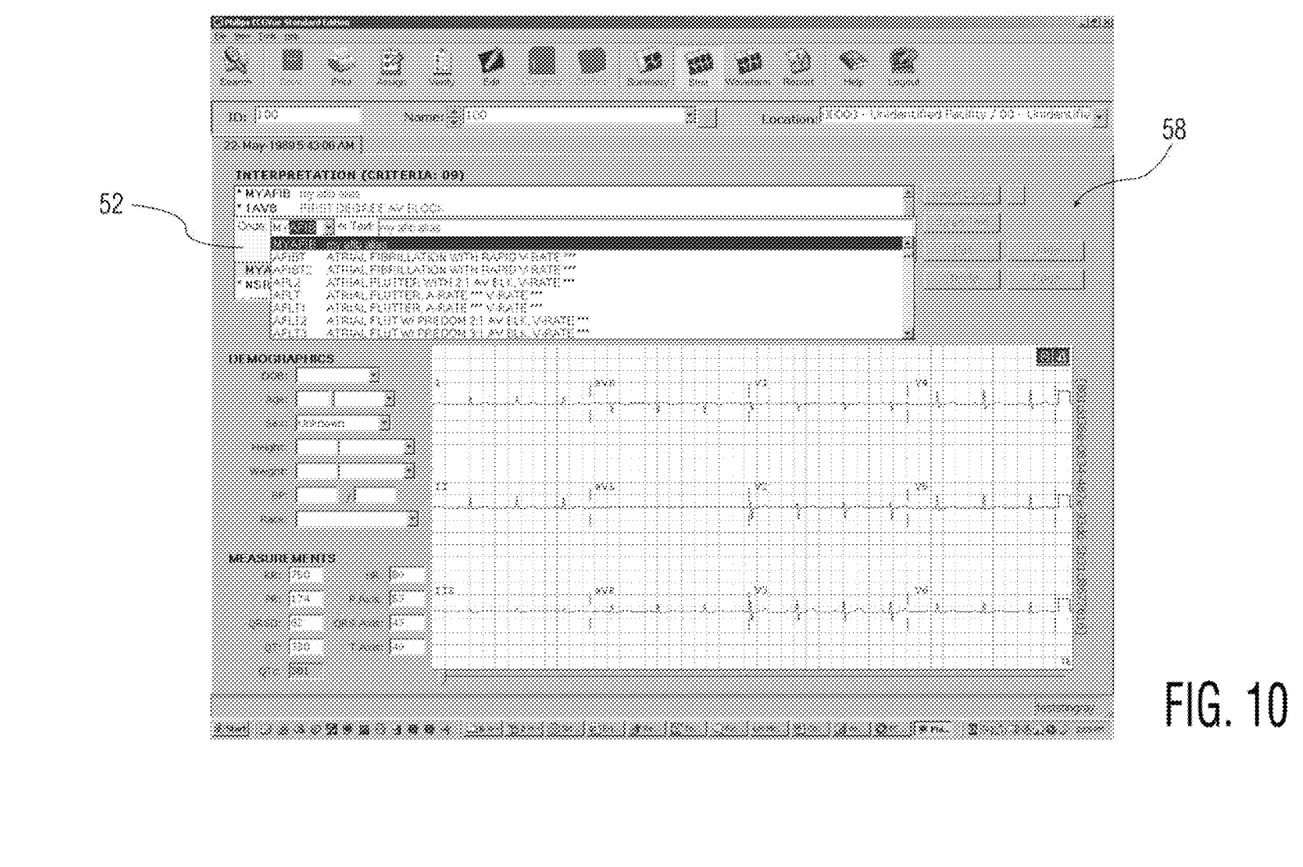
FIG. 10 illustrates a display screen of an ECG data management system in which a customized codes in a list of preferred codes is being added to the ECG interpretation by typing in the code.
Figure 11:
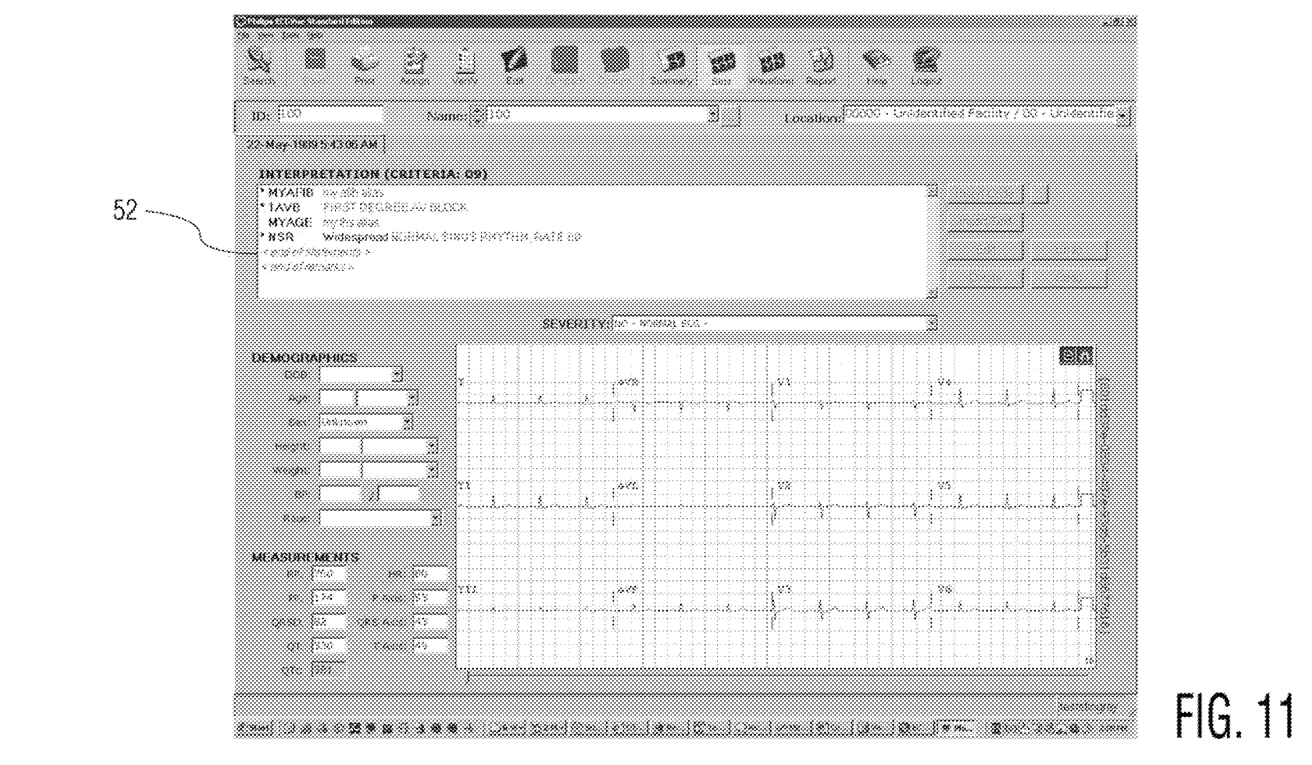
FIG. 11 illustrates an interpretation view on an ECG data management system screen of a finished report.

In use, the user can open an interpretation dialog box 52a, in which the diagnosis is composes. The user can then open his or her favorites list 56. When the user double-clicks on a code line, that line appears in the interpretation dialog box. In this example the user can also enter codes and statements directly into the interpretation box 52 by positioning a cursor in the box and typing in a code. As FIG. 10 illustrates, in this example as the user begins to type in a code, the ECG data management system will use "intellisense" to fill in the remainder of a code which matches the user's typed letters. In FIG. 10 the user has typed the first two letters of "MYAFIB," and the system matches and fills in the complete alias MYFIB code and its statement. The user can also use the editing buttons 58 to the right of the interpretation box 52 to enter free-form text and information into the interpretation box of the report. FIG. 11 shows a finished ECG diagnostic report which includes both standard, factory-supplied codes and statements 1AVB and NSR, and the alias codes MYAFIB and MYAGE and their associated alias statements.

Figure 12:
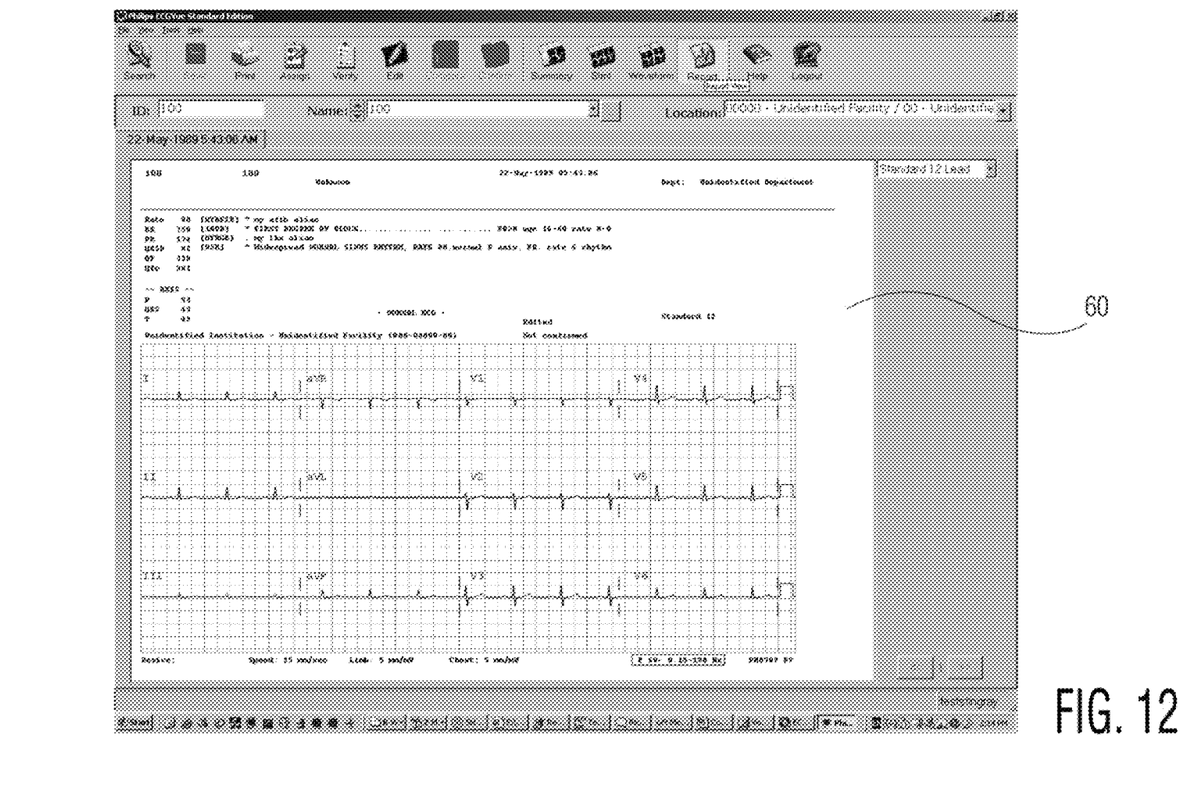
FIG. 12 illustrates a finished ECG diagnostic report in the print preview mode.

FIG. 12 illustrates a finished ECG report 60 which is ready for distribution to physicians over the ECG data management system. In this example the report 60 is shown in the report preview mode, illustrating how the report will look after it has been printed.

What is claimed is:

1. An electrocardiogram (ECG) data management system for managing diagnostic ECG codes and associated statements comprising:
 a database of one or more groups of ECG codes and statements including factory-provided ECG codes and statements implemented in a computer-readable medium;
 a database manager having a user interface and a display by which an administrator can edit a group of ECG codes and statements to include (i) the factory-provided ECG codes and statements and (ii) alias ECG codes and statements, selected for use in a facility; and
 a mapping processor which automatically maps ECG codes provided by an ECG device to the edited group of ECG codes and statements selected for use in the facility, wherein the ECG codes provided by the ECG device and the edited group of ECG codes and statements selected for use in the facility are different but represent the same ECG characteristic.

2. The ECG data management system of claim 1, wherein the database further comprises a master list of ECG codes and statements from which an administrator can select ECG codes and statements for a facility list to be used in the facility.

3. The ECG data management system of claim 2, wherein the database manager enables the editing of the master list by selecting a subset of all ECG codes and statements of the master list for the facility list.

4. The ECG data management system of claim 3, wherein the database manager further enables the editing of the master list by the addition of alias codes for the facility list.

5. The ECG data management system of claim 3, wherein the database manager further enables the editing of the master list by the addition of alias codes and statements for the facility list.

6. The ECG data management system of claim 2, further comprising a system setting by which an administrator can implement ECG codes of a facility list for use by users of the ECG data management system.

7. The ECG data management system of claim 2, further comprising a system setting by which an administrator can implement ECG codes and statements of a facility list for use by users of the ECG data management system.

8. The ECG data management system of claim 2, wherein the ECG data management system is operable with different ECG devices,
 wherein the mapping processor operates to replace ECG codes or statements provided by an ECG device with ECG codes or statements of the facility list.

9. The ECG data management system of claim 8, further comprising an editor, coupled to the database and responsive to ECG codes or statements provided by an ECG device, by which the ECG codes or statements provided by an ECG device can be edited.

10. The ECG data management system of claim 9, wherein the editor is operable to modify, delete, or add to the ECG codes or statements provided by an ECG device.

11. An electrocardiogram (ECG) data management system for managing diagnostic ECG codes and associated statements comprising:
 a database of one or more groups of ECG codes and statements including a master list of ECG codes and statements implemented in a computer-readable medium; and
 an editor having a user interface and a display by which a user can assemble a favorites list of selected ECG codes and statements from the master list,
 wherein the editor is operable to select factory-provided ECG codes or statements or alias ECG codes or statements from the master list, and further wherein the factory-provided ECG codes or statements and alias ECG codes or statements from the master list are different but represent the same ECG characteristic,
 wherein the editor is operable to edit a favorites list during the editing of an ECG diagnostic report by selecting a plurality of the ECG codes or statements from a displayed selection box of the master list.

12. The ECG data management system of claim 11, wherein the database is operable to store a favorites list assembled by a user,
   wherein the stored favorites list can be recalled by the user when accessing the ECG data management system.

13. The ECG data management system of claim 11, further comprising a report viewer by which a user can view or edit an ECG report,
   wherein a user can add an ECG code of a favorites list to the ECG report by clicking on the ECG code in a favorites list.

14. The ECG data management system of claim 11, further comprising a report viewer by which a user can view or edit an ECG report,
   wherein a user can add an ECG code of a favorites list to the ECG report by typing at least one letter of an ECG code of the favorites list.

\* \* \* \* \*